United States Patent [19]

Ashworth et al.

[11] Patent Number: 4,951,873
[45] Date of Patent: Aug. 28, 1990

[54] MULTI-LINE ELECTRONIC MEDIA BARRIER

[75] Inventors: John Ashworth, Canton; Thomas Ingve, Redford, all of Mich.

[73] Assignee: Graco Robotics, Inc., Livonia, Mich.

[21] Appl. No.: 338,046

[22] Filed: Apr. 14, 1989

[51] Int. Cl.⁵ .............................................. G01R 27/26
[52] U.S. Cl. ....................................... 239/67; 239/72; 137/2; 137/467.5; 324/689
[58] Field of Search ....................... 239/67, 63, 71, 72; 137/467.5, 456, 2; 324/61 R

[56] References Cited

U.S. PATENT DOCUMENTS

| | | | |
|---|---|---|---|
| 2,666,148 | 1/1954 | Arvintz et al. | 137/2 |
| 2,882,914 | 4/1959 | Wiley et al. | 137/2 |
| 4,074,184 | 2/1978 | Dechene et al. | 324/61 R |
| 4,240,028 | 12/1980 | Davis, Jr. | 324/61 R |
| 4,552,164 | 11/1985 | Urella | 137/2 |
| 4,751,842 | 6/1988 | Ekrann et al. | 324/61 R |
| 4,769,593 | 9/1988 | Reed et al. | 324/61 R |

FOREIGN PATENT DOCUMENTS 2129525  4/1984  United Kingdom ............. 137/467.5

Primary Examiner—Andres Kashnikow
Assistant Examiner—Christopher G. Trainor
Attorney, Agent, or Firm—Paul L. Sjoquist

[57] ABSTRACT

A multi-line electronic media barrier or safety system for preventing liquid contamination of air lines, including a capacitance proximity sensor for detecting a foreign undesirable medium such as paint in an air line. When foreign media is detected, a main air valve is closed which in turn closes valves connected in the air lines, thereby blocking passage of air or liquid and protecting pneumatic control apparatus. The media barrier is especially designed for use with automated or robotic paint spray devices utilized in industry.

8 Claims, 2 Drawing Sheets

MULTI-LINE ELECTRONIC MEDIA BARRIER

BACKGROUND OF THE INVENTION

The present invention relates to safety systems for detecting liquid contaminants in pneumatic lines and closing the lines in response thereto and, more particularly, to safety systems in pneumatic control lines which control valving associated with liquid delivery systems such as automated paint spray apparatus.

In a liquid delivery system such as a pneumatically controlled robotic paint spray system, low pressure air lines share valve interfaces with high pressure liquid containing lines delivering paint to be sprayed. For example, in automated paint spray delivery systems the pneumatic control pressures are usually industrial air lines operating at or below 100 pounds per square inch (psi), and the liquid lines typically deliver paint and solvents at pressures in a range from 150 psi to 1500 psi.

The difference in pressure between the pneumatic and liquid lines may cause contamination of the pneumatic control system. If a defect occurs at one of the valve interfaces between the pneumatic and liquid systems, the greater liquid pressure will cause liquid to flow into and through the pneumatic lines. If left uncontrolled, this liquid flow would eventually fill the pneumatic lines and contaminate the entire pneumatic system, destroying all or most of the pneumatic control apparatus. Such a contamination problem is especially acute in automated systems, which are frequently unattended for extended periods of time, and in which a valving or interface defect could literally shut down and destroy an entire paint spraying station and thereby disable or render malfunctional one or more automatic paint spraying robots.

Moreover, in automated factories such as automobile plants, the problem of a malfunctioning paint spraying robot may be readily compounded into larger problems. If a robot fails to apply paint to the body of a car or a part thereof, that particular body or part may be mismatched with parts subsequently added further down the assembly line. Hence an entire car factory may be shut down because of a relatively minor defect in a paint spray valving system.

SUMMARY OF THE INVENTION

An object of the present invention is to provide a safety system for detecting liquid contaminants in pneumatic lines.

Another object of the present invention is to provide a safety system for closing the pneumatic lines when liquid contaminants are sensed.

A feature of the present invention includes a capacitance proximity sensor positioned in close physical proximity to one or more pneumatic control lines to sense a change in capacitance within the lines. Since the capacitance of air is different from the capacitance of a liquid such as paint, a change in capacitance may indicate contamination. The sensor is electrically coupled to a valve shut-off system, an audible alarm, and a visual indicator, all of which may operate when a predetermined amount of change in the capacitance is sensed.

An advantage of the present invention is that foreign, contaminating liquids in a pneumatic control line are immediately sensed.

Another advantage of the present invention is that the sensor responds to the existence of liquid by readily closing a pneumatic control valve before expensive pneumatic control apparatus is contaminated.

Another advantage of the present invention is that mechanical in-line sensors are absent.

Another advantage of the present invention is that it may be integrated into existing automated spray stations with little or no change in the structure or function of the robotic systems.

Another advantage of the present invention is that it is inexpensive to manufacture and simple to operate.

DETAILED DESCRIPTION OF THE PREFERRED EMBODIMENT

Figure 1:
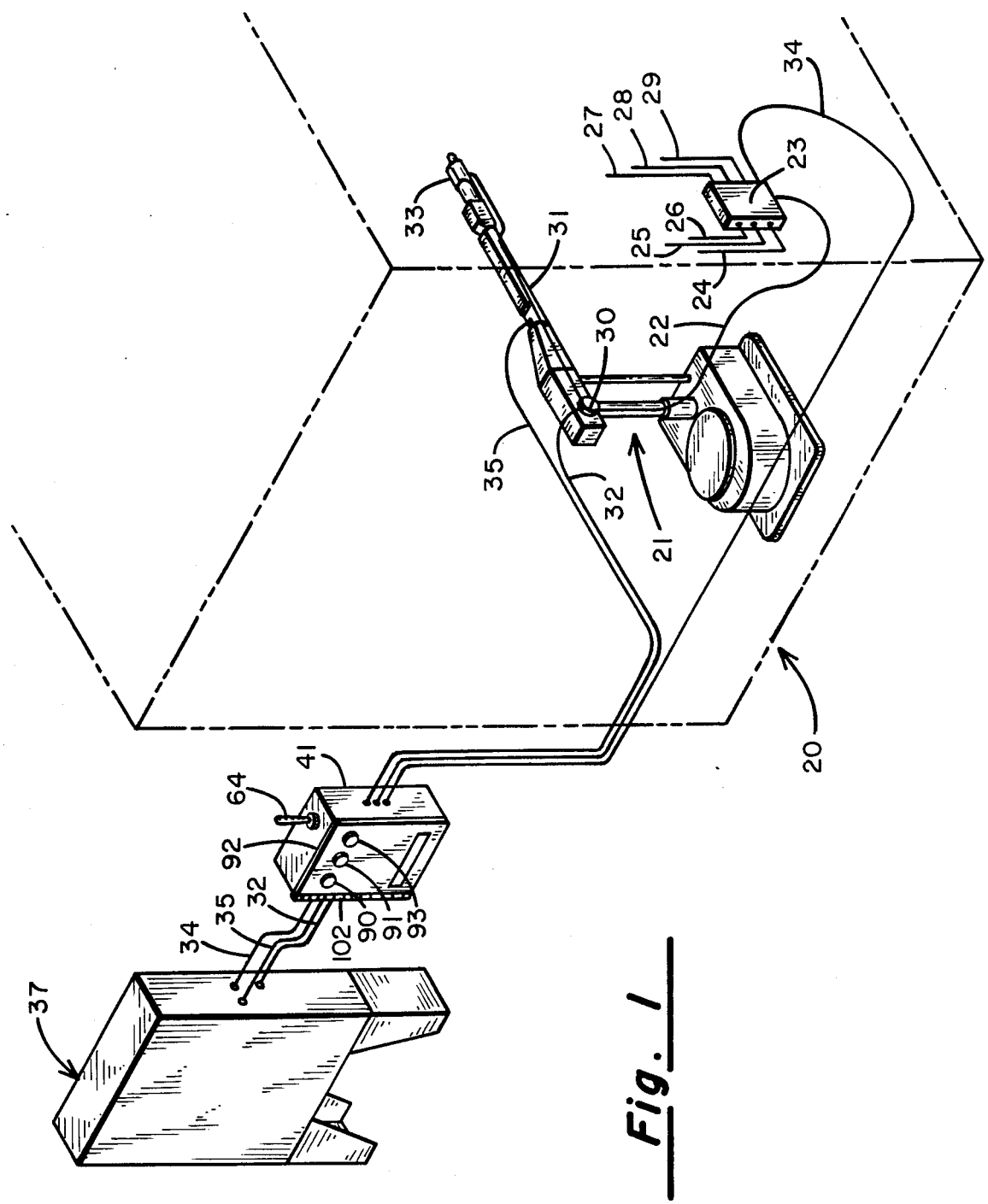
FIG. 1 is a typical isometric view showing a pneumatic control panel, pneumatic control lines, electronic media barrier housing for the safety system for sensing and responding to the presence of liquid contaminates, and a spray booth having a spray gun, a fluid pressure regulator, a color changer fluid valve and fluid lines.

The present invention, a multi-line electronic media barrier or a safety system for detecting liquid contaminants in pneumatic lines and closing the lines thereto, is generally indicated by reference numeral 10 in FIG. 1. FIG. 1 shows the environment of the media barrier or safety system 10.

As shown by FIG. 1, a spray booth 20 includes a robotic spray assembly 21 receiving liquid such as paint or a solvent/air mixture from hose 22 connected to a color changer valve stack 23. The valve stack 23 receives liquid from any one of six lines 24, 25, 26, 27, 28 and 29. Each of the lines 24–29 typically provides paint of a different color, or a cleaning solvent, to the color changer valve stack 23. A flushing air line 34 is also connected to the color changer valve stack 23.

Liquid line 22 is connected to a pressure regulator 30 affixed to the robotic spray assembly 21. The regulator 30 controls the pressure of liquid in a spraying line 31 and hence controls the pressure at which liquid such as paint is sprayed on an object such as an automobile. The pressure regulator 30 is controlled pneumatically by a pneumatic control line 32.

The spraying of a liquid such as paint through the spray nozzle 33 is controlled by a spray valve in the spray nozzle 33. The spray valve in turn is controlled pneumatically by the pneumatic control line 35, to regulate the paint spraying operation.

The pneumatic control lines 32, 34 and 35 extend from the spray booth 20 to and through the electronic media barrier or safety system 10 to a pneumatic control panel enclosure 37. Besides enclosing a control panel, the enclosure 37 may include pneumatic control lines for other spray booths and for other equipment.

Figure 2:
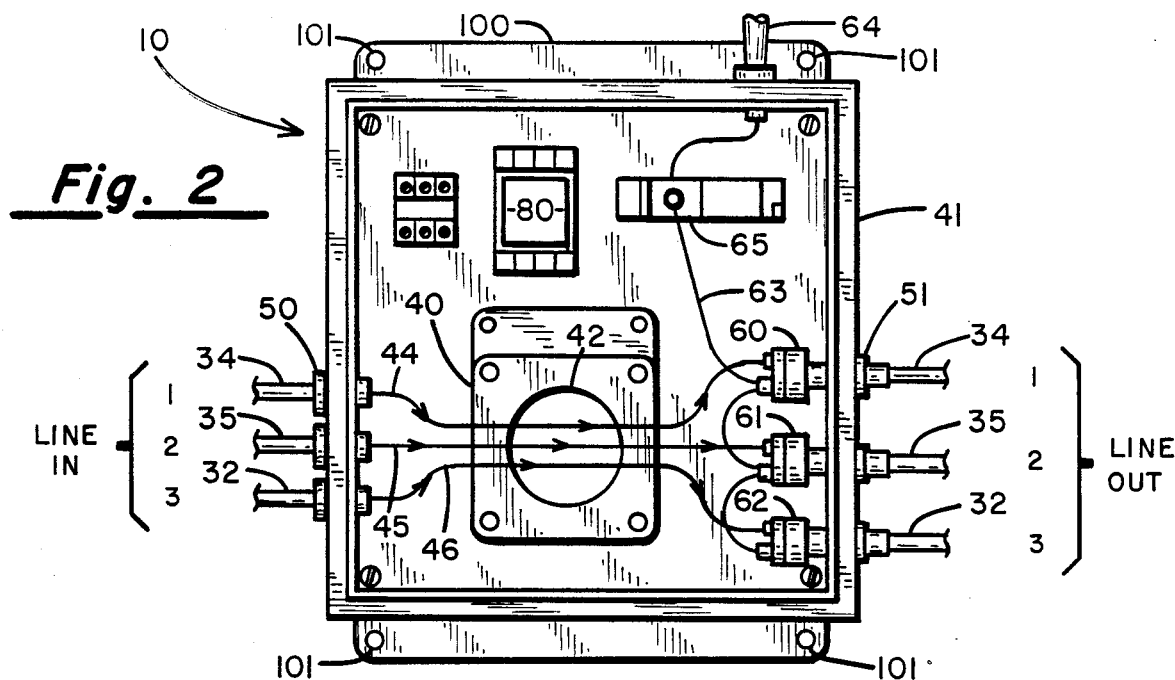
FIG. 2 shows a partially broken apart, partially phantom, elevational view of the multi-line electronic media barrier.
Figure 3:
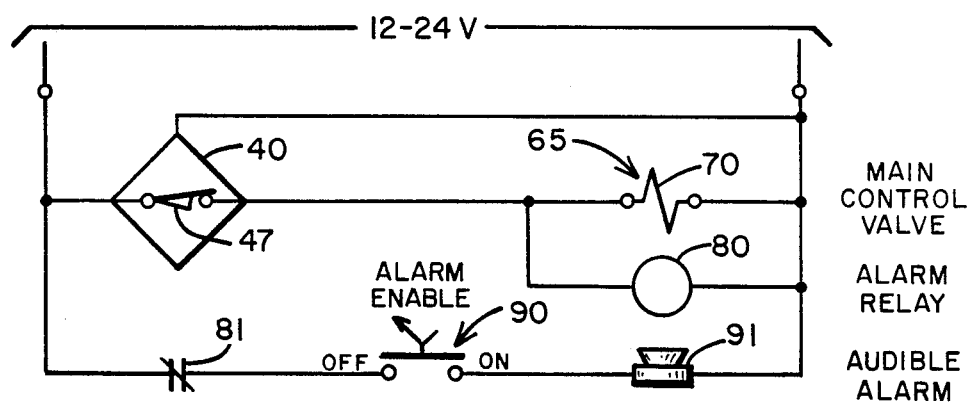
FIG. 3 is an electrical schematic of the multi-line electronic media barrier.

As shown by FIG. 2, the safety system or multi-line electronic media barrier 10 includes a capacitance proximity sensor 40 affixed in a housing 41. A planar capacitance sensing head 42 of the sensor 40 is disposed in close proximity with a set of planar tubular segments 44, 45, 46 corresponding, for example, to each of the pneumatic control lines 32, 34 and 35. The planar segments 44, 45, 46 are secured across the planar capacitance sensing head 42 and are also in close physical proximity and in a planar alignment. When the tubular pneumatic segments 44, 45 and 46 are empty or when air is passing therethrough, a switch 47 in the sensor 40 is closed, as shown in FIG. 3. The sensor 40 includes a potentiometer (not shown) which may be set so that the sensor 40 effectively ignores the density of the tubular line segments 44, 45, 46. When liquid such as paint or paint solvent or other dense media travels across the sensor through the tubular line segments 44, 45, 46, the switch 47 opens.

Each of the incoming line portions of lines 32, 34 and 35 is secured to the electronic media barrier housing 41 by a first threaded line connector 50. Each of the outgoing line portions of lines 32, 35, 36 is secured to the housing 41 by a second threaded line connector 51.

Figure 4:
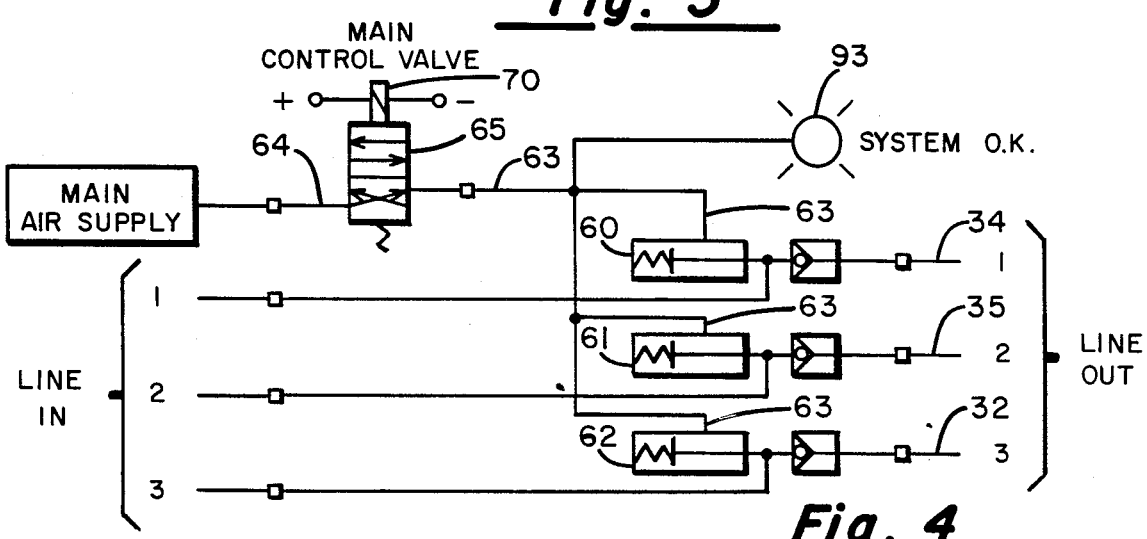
FIG. 4 is a pneumatic schematic of the multi-line electronic media barrier.

A set of three air piloted fluid valves 60, 61, 62 are affixed in the electronic media barrier housing 41 and are in line with respective pneumatic control lines 32, 34 and 35 and respective planar line segments 44, 45, 46. Each of the piloted fluid valves 60, 61, 62 is also in line with and controlled by a control air line 63, as shown in FIG. 4. The control air line 63 conveys air from a main air supply 64 to the valves 60, 61, 62. When air pressure is being supplied via line 63 to the valves 60, 61, 62, the valves 60, 61, 62 are open and allow air to be conveyed through the pneumatic control lines 32, 34 and 35. When the supply of air to the valves 60, 61, 62 is cut off, such as when a solenoid operated main control valve 65 is closed, the valves 60, 61, 62 close to prevent passage of medium such as liquid or air through pneumatic control lines 32, 34 and 35.

The solenoid operated main control valve 65 is affixed in housing 41 and electrically coupled to the capacitance proximity sensor 40, as shown in FIG. 3. A solenoid 70 of the main valve 65 is electrically coupled to the switch 47 of the sensor 40. When the switch 47 is closed, the solenoid is energized and the main control valve 65 is open. When the switch 47 is opened, such as when the sensor 40 detects liquid in one of the line segments 44, 45, 46, the solenoid 70 is de-energized, thereby closing the main control valve 65, as shown in FIG. 4.

The sensor 40 is electrically coupled to an alarm relay 80 set in the electronic media barrier housing 41. When switch 47 of the sensor 40 is closed, a switch 81 of the alarm relay 80 is open. When switch 47 is opened, such as when liquid is detected by the sensor 40, the switch 81 of the alarm relay 80 is closed, as shown in FIG. 3.

The alarm relay switch 81 is electrically coupled to an alarm enable or toggle switch 90, which in turn is connected to an audible alarm or horn 91. The alarm enable 90 and the audible alarm 91 are affixed to a cover 92 of the housing 41.

A pneumatic indicator 93 is affixed in the cover 92 and is mounted downstream from the main control valve 65, as shown in FIG. 4. When the main control valve 65 is energized, the pneumatic indicator 93 is deactivated. When the main control valve 65 is deenergized, such as when liquid is present in line segments 44, 45, 46, the pneumatic indicator 93 is deactivated by the absence of air flow and indicates in a visual fashion the presence of contaminating liquid.

It should be noted that electronic barrier media housing 41 includes an apertured back plate 100 with a set of four apertures 101 for being mounted on a structure such as a wall. The cover 92 includes a hinge 102 for connection to the housing 41.

It should further be noted that the capacitance proximity sensor 40 may be a three-wire direct current proximity switch such as one sold by Efector, Inc., located in Prussia, Pennsylvania, having a part number KDE-3060-FPKG. The 3-wire DC, positive switching sensor 40 typically has an adjustable, nonshielded nominal detection range of 60 mm, an operating supply of 5 mA at 24v, and a maximum load current allowable during continuous operation of 250 mA. The housing of the switch 40 is oil and dust tight, splash proof, and resistant to liquids such as paints and paint solvents. The housing may be formed of the plastic known by the acronym PPG (NORYL) and may have a NEMA rating of 3, 4, 12, 13 and an IP rating of 65.

In operation, when the pneumatic control lines 32, 34 and 35 are conveying air from the pneumatic control panel enclosure 37 to the robotic spray assembly 21 and the capacitance proximity sensor 40 detects no liquid in the planar line segments 44, 45, 46, the sensor switch 40 is closed so that the solenoid 70 is energized, thereby maintaining the main control valve 65 in a passing condition. With the main control valve 65 passing, air to the air piloted fluid valves 60, 61, 62, which are thereby maintained in an open position, this allows passage of air in pneumatic control lines 32, 34 and 35 from the electronic media barrier housing 41 to the spray assembly 21 and to the color changer valve stack 23.

Paint or paint solvents may contaminate one or more of the pneumatic control lines 32, 34 and 35 when a defect occurs in the color changer 23, pressure regulator 30, spray nozzle 33, or other like interface. A typical defect is a faulty interfacing valve in the color changer 23, pressure regulator 30, or spray nozzle 33, all of which may be controlled by a pneumatic control line such as one of the lines 32, 34 and 35. Since paint is usually under a greater pressure than the air in the pneumatic control lines, paint or paint solvents will be forced toward the electronic media barrier or safety system 10.

When the capacitance proximity sensor 40 detects liquid such as paint or paint solvents in one of the planar line segments 44, 45, 46, the sensor switch 47 is opened, thereby de-energizing the solenoid 70 of the main control valve 65. When the solenoid is de-energized, the main control valve 65 closes and cuts off the flow of air to the air piloted fluid valves 60, 61, 62, which are thereby closed. When the valves 60, 61, 62 are closed, the pneumatic control lines 32, 34 and 35 are blocked as to the passage of media such as air or liquid and hence the pneumatic control panel 37 is protected from contamination.

Simultaneously with the closing of the valves 60, 61, 62, an operator may be visually and audibly notified. When the capacitance proximity sensor 40 detects foreign media such as paint and the sensor switch 47 opens, the alarm relay 80 closes a switch 81. When the switch 81 is closed, a horn 91 will be energized if the alarm enable or toggle switch 90 has been turned to an on position. When the sensor switch 47 opens to de-energize the solenoid 70 and close the main control valve 65, air flow is cut off to the pneumatic indicator 93 which is thereby energized to indicate visually the presence of liquid or other media in the planar line segments 44, 45, 46.

It should be noted that although the potentiometer of the capacitance proximity sensor 40 may be set so as to detect extremely small quantities of liquid such as the water present in humid air, it may be desirable to adjust the sensor 40 to ignore such small quantities of liquid. Furthermore, although the sensor 40 may be adjusted to ignore tubing such as the planar line segments 44, 45, 46, it may be desirable to avoid the use of extremely small air lines.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A safety system for detecting foreign media in pneumatic lines and for closing the lines in response thereto, comprising:
   (a) a pneumatic line,
   (b) a capacitive sensor positioned adjacent the pneumatic line for sensing the presence of foreign media in the pneumatic line, the sensor having means for generating a control signal upon the sensing of the foreign media in the pneumatic line, and
   (c) valve means interposed into said pneumatic line and coupled to said sensor, for controlling flow through said pneumatic line, wherein the valve means includes a main control valve electrically coupled to the sensor and a second pneumatically operated valve connected in the pneumatic line, the main control valve controlling the flow of air from an air supply to the second pneumatically operated valve and thereby controlling the second pneumatically operated valve, the main control valve being closed and shutting off the supply of air to the second pneumatically operated valve when the sensor senses foreign media in the line and sends the control signal to the main control valve, the second valve being closed and thereby blocking passage of air or foreign media through the pneumatic line when the main control valve closes and shuts off the supply of air to the second valve; the valve means providing for the flow blockage of the pneumatic line upon the receipt of said control signal from said sensor.

2. The system of claim 1, wherein said pneumatic line includes a first planar segment and said capacitance sensor includes a planar sensing head, the planar segment being positioned in close physical proximity to the planar sensing head.

3. The system of claim 2, further comprising at least one additional pneumatic line having a second planar segment, the respective planar segments positioned in planar alignment in close physical proximity, the planar segments disposed adjacent the planar sensing head.

4. The system of claim 1, further comprising at least one additional pneumatic line and a third pneumatically operated valve connected in the additional pneumatic line, the main control valve controlling air flow to the third pneumatically operated valve and thereby controlling the third pneumatically operated valve, the second and third valves being operated simultaneously by the main control valve, and both of the valves being closed in response to the presence of foreign media in one of the lines.

5. The system of claim 1, further comprising an audible alarm electrically coupled to the sensor for receiving the control signal generated by the sensor when foreign media is present in the line, the alarm being energized and audible upon receipt of the control signal.

6. The system of claim 1, further comprising a pneumatic visual indicator pneumatically coupled to the valve means and operated thereby upon the closing of the valve means, the absence of air flow to the indicator generating a visual signal to indicate the presence of foreign media in the pneumatic line.

7. A multi-line electronic media barrier for being positioned between a pneumatic control apparatus and a paint spray apparatus such as a robotic spray gun wherein the paint spray apparatus has fluid valves controllable by the pneumatic control apparatus, comprising:
   (a) a set of pneumatic control lines connected between the pneumatic control apparatus and the paint spray apparatus, each of the lines having a planar segment, the planar segments being positioned in planar alignment and in close physical proximity,
   (b) a capacitance sensor having a planar sensing head, the capacitance sensor being disposed between the pneumatic control apparatus and the paint spray apparatus, the planar sensing head being positioned immediately adjacent the planar segments, the sensor sensing the presence of foreign media in the pneumatic lines, the sensor having means for generating a control signal upon the sensing of the foreign media,
   (c) a main control valve electrically coupled to the sensor for providing for the closing of the pneumatic control lines upon receipt of the control signal from the sensor indicating the presence of foreign media in at least one of the lines, the main control valve being disposed in a main air supply line downstream from a main air supply, and
   (d) a set of media blocking valves, each of the valves disposed in a respective pneumatic control line downstream from the planar segments for closing the lines to the passage of air or foreign media, the valves being pneumatically coupled to the main air supply and operated by the main control valve so that when the sensor senses the presence of foreign media in one of the pneumatic control lines, the sensor generates the control signal, the main control valve being de-energized and closed upon receipt of the control signal and thereby closing the main air supply line and shutting off the supply of air to the set of media blocking valves which close in response thereto and block the passage of air or foreign media through the pneumatic control lines whereby contamination of the pneumatic control apparatus by foreign media such as paint is prevented.

8. A safety system for detecting liquid contaminants in pneumatic lines and for closing the lines in response thereto, comprising
   (a) a plurality of pneumatic lines having at least one segment wherein all the pneumatic lines are arranged in a group, wherein the lines at the segment are positioned in planar alignment in close physical proximity;
   (b) a capacitive sensor having a planar sensing head bridging across said group of lines, said sensing head positioned immediately adjacent said pneumatic lines' planar alignment segment; and said sensor having means for generating a control signal upon detection of liquid in any said pneumatic lines' planar alignment segment;
   (c) a pneumatic control valve operatively connected to control pneumatic flow through said pneumatic lines; and
   (d) means for coupling said sensor means for generating a control signal to said pneumatic control valve.

* * * * *